United States Patent
Ptock et al.

(10) Patent No.: US 6,362,192 B1
(45) Date of Patent: Mar. 26, 2002

(54) 2-(PYRAZOLYLOXY)-PYRIDIN-3-YLACETIC ACID DERIVATIVES, AGENTS CONTAINING THE SAME AND USE THEREOF AGAINST NOXIOUS FUNGI AND ANIMAL PARASITES

(75) Inventors: Arne Ptock, Ludwigshafen; Hubert Sauter, Mannheim; Reinhard Kirstgen, Neustadt; Wassilios Grammenos, Ludwigshafen; Thomas Grote, Schifferstadt; Andreas Gypser; Herbert Bayer, both of Mannheim; Markus Gewehr, Kastellaun; Oliver Cullmann, Mannheim; Bernd Müller, Frankenthal; Roland Götz, Ludwigshafen; Franz Röhl, Schifferstadt; Eberhard Ammermann, Heppenheim; Gisela Lorenz, Neustadt; Volker Harries, Frankenthal; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,885
(22) PCT Filed: Jan. 26, 1999
(86) PCT No.: PCT/EP99/00470
   § 371 Date: Jul. 6, 2000
   § 102(e) Date: Jul. 6, 2000
(87) PCT Pub. No.: WO99/40082
   PCT Pub. Date: Aug. 12, 1999

(30) Foreign Application Priority Data

Feb. 5, 1998 (DE) .................. 198 04 486

(51) Int. Cl.[7] ............ A01N 43/54; A01N 43/40; C07D 401/00; C07D 213/04; C07D 239/02
(52) U.S. Cl. ............ 514/269; 514/333; 514/341; 544/298; 544/333; 544/334; 544/335; 546/255; 546/276.1
(58) Field of Search ............ 558/408; 514/163, 514/164, 165, 618, 670, 532, 533, 269, 333, 341; 560/17, 43, 60, 81, 104; 546/255, 776.1; 544/298, 333, 334, 335

(56) References Cited

U.S. PATENT DOCUMENTS 5,298,527 A   3/1994  Grammenos ............ 514/333
5,395,854 A   3/1995  Brand et al. ............ 514/333
5,416,068 A * 5/1995  Grammenos ............ 504/378
5,516,804 A * 5/1996  Brand et al. ............ 514/414
5,523,454 A * 6/1996  Brand et al. ............ 558/408

FOREIGN PATENT DOCUMENTS

| CA | 1 177 081 | 10/1984 | ............ 546/276.1 |
| EP | 477 631 | 4/1992 | ............ 546/276.1 |
| EP | 513 580 | 11/1992 | ............ 546/276.1 |
| EP | 579 071 | 1/1994 | ............ 546/276.1 |
| FR | 2452493 | 10/1980 | ............ 546/276.1 |
| WO | 95/06033 | 3/1995 | ............ 546/276.1 |
| WO | 97/24332 | 6/1997 | ............ 546/276.1 |
| WO | 97/24316 | 7/1997 | ............ 546/276.1 |
| WO | 97/29093 | 8/1997 | ............ 546/276.1 |
| WO | 98/12179 | 3/1998 | ............ 546/276.1 |

* cited by examiner

Primary Examiner—Alan L. Rotman
Assistant Examiner—Raymond Covington
(74) Attorney, Agent, or Firm—Keil & Weinkauf

(57) ABSTRACT

Compounds of the formula I

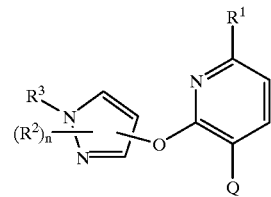

(I)

and salts thereof, in which the substituents and the index n have the following meanings:

Q is —C(=CHCH$_3$)—COOCH$_3$,
   —C(=CHOCH$_3$)—COOCH$_3$,
   —C(=NOCH$_3$)—COOCH$_3$ or
   —C(=NOCH$_3$)—CONH(CH$_3$);

$R^1$ is hydrogen, halogen, $C_1$–$C_4$-alkyl, $C_1$–$C_2$-haloalkyl, $C_1$–$C_4$-alkoxy or $C_1$–$C_2$-haloalkoxy;

$R^2$ is halogen, $C_1$–$C_4$-alkyl, $C_1$–$C_2$-haloalkyl, $C_1$–$C_4$-alkoxy;

n is 0, 1 or 2, where the substituents $R^2$ may be different if n=2;

$R^3$ is phenyl, pyridyl or pyrimidyl, compositions comprising them and the use of the compounds I and the compositions for controlling harmful fungi and animal pests are described.

8 Claims, No Drawings

2-(PYRAZOLYLOXY)-PYRIDIN-3-YLACETIC ACID DERIVATIVES, AGENTS CONTAINING THE SAME AND USE THEREOF AGAINST NOXIOUS FUNGI AND ANIMAL PARASITES

The present invention relates to compounds of the formula I

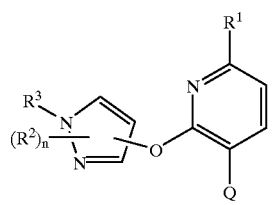

(I)

and salts thereof, in which the substituents and the index n have the following meanings:

Q is —C(=CHCH$_3$)—COOCH$_3$,
—C(=CHOCH$_3$)—COOCH$_3$,
—C(=NOCH$_3$)—COOCH$_3$ or
—C(=NOCH$_3$)—CONH(CH$_3$);

R$^1$ is hydrogen, halogen, C$_1$–C$_4$-alkyl, C$_1$–C$_2$-haloalkyl, C$_1$–C$_4$-alkoxy or C$_1$–C$_2$-haloalkoxy;

R$^2$ is halogen, C$_1$–C$_4$-alkyl, C$_1$–C$_2$-haloalkyl, C$_1$–C$_4$-alkoxy;

n is 0, 1 or 2, where the substituents R$^2$ may be different if n=2;

R$^3$ is phenyl, pyridyl or pyrimidyl, where the phenyl, pyridyl or pyrimidyl radical may carry one or, independently of one another, two or three of the following substituents: halogen, cyano, C$_1$–C$_4$-alkyl, C$_1$–C$_2$-haloalkyl, C$_1$–C$_4$-alkoxy, C$_1$–C$_2$-haloalkoxy or C$_1$–C$_4$-alkoxycarbonyl.

Patent EP-A 579 071 describes, in a general way, hetaryl acetic acids, in particular those having a 5-ring-hetaryl radical, as crop protection agents. Pyridin-3-ylacetic acid derivatives which are substituted in position 2 and have fungicidal activity are described in WO-A 95/06033 and WO-A 98/12179. WO-A 98/12179 additionally mentions an activity of the compounds claimed against animal pests.

Finally, WO-A 97/24332 discloses phenylacetic acid derivatives having a pyrazolyloxy substituent ortho to the acetic acid group which are active against harmful fungi and animal pests.

However, with respect to the activity spectra and application rates, the prior art compounds of this type are not satisfactory.

It is an object of the present invention to provide improved active compounds against harmful fungi and animal pests.

We have found that this object is achieved by the compounds I defined at the outset and their salts.

Furthermore, we have found compositions for controlling harmful fungi and animal pests which comprise the compounds I or salts thereof, and the use of the compounds I and salts thereof and of the compositions comprising them for this purpose.

The compounds I can be obtained a variety of ways by processes known per se. In principle, it is immaterial during their synthesis whether the pyrazolyloxy radical in position 2 or the grouping "Q" in position 3 at the pyridine ring is constructed first.

The compounds I are obtainable for example via the compounds Z (Synthetic route 1) which for their part are obtainable by reaction of compounds of the formula II with hydroxypyrazoles of the formula III.

Synthetic route 1:

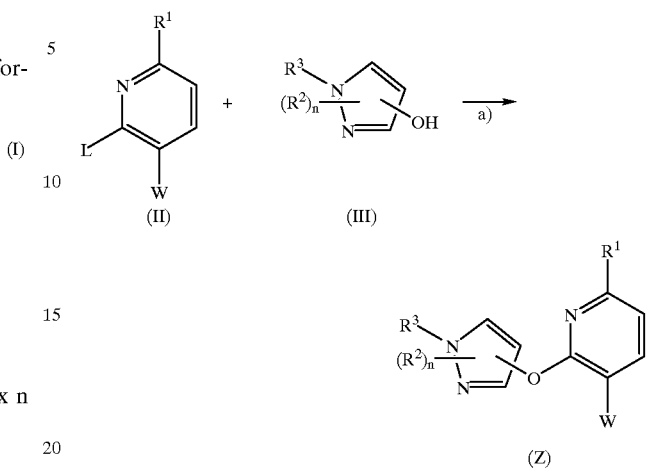

where:
L is a leaving group customary for nucleophilic aromatic substitution, such as fluorine, chlorine, bromine or the nitro group and, in particular, chlorine or fluorine;
W is a group which makes possible or facilitates the nucleophilic exchange of the group L and which additionally—as described below—can be converted into the group Q of the compounds I, eg.: —CO—CO—OR', —CO—CO—NHR', —CO—OR' or —CO—CH$_3$ (R'=C$_1$–C$_4$-alkyl), in particular —CO—CO—OCH$_3$.

1a) This reaction is usually carried out at 0–120° C., preferably at 20–60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, and dimethyl sulfoxide, dimethylformamide, dimethylacetamide, 1,3-dimethylimidazolidin-2-one and 1,3-dimethyltetrahydro-2(1H)-pyrimidinone; particular preference is given to dimethyl sulfoxide, dimethylacetamide and dimethylformamide.

It is also possible to use mixtures of the abovementioned solvents.

In general, suitable bases are: basic, inorganic compounds, for example alkali metal and alkaline earth metal hydrides such as lithium hydride, sodium hydride, potassium hydride, calcium hydride, alkali metal and alkaline earth metal carbonates such as potassium carbonate and calcium carbonate, furthermore silver carbonate and alkali metal bicarbonates such as sodium bicarbonate, organometallic compounds and alkali metal and alkaline earth metal alkoxides such as potassium methoxide, potassium tert-butoxide and dimethoxymagnesium. Organic bases, for example tertiary amines such as trimethylamine, triethylamine, diisopropylethylamine and n-methylpiperidine, pyridine, substituted pyridines such as collidine, lutidene and 4-dimethyl-aminopyridine and bicyclic amines are also suitable. Particular preference is given to sodium hydride, potassium carbonate and potassium tert-butoxide.

The bases are generally employed in equimolar amounts or, if appropriate, as solvent.

For the reaction, it may be advantageous initially to treat the compounds III with base and to react the resulting salt with the compound II.

Furthermore, it may be advantageous for the reaction to add a catalytic amount of a crown ether such as, for example, 18-crown-6 or 15-crown-5 or any other customary phase-transfer catalyst.

Suitable for use as phase-transfer catalysts are ammonium halides and ammonium tetrafluoroborates such as benzyltriethylammonium chloride, benzyltributylammonium bromide, tetrabutylammonium chloride, hexadecyltrimethylammonium bromide or tetrabutylammonium tetrafluoroborate and phosphonium halides such as tetrabutylphosphonium chloride or tetraphenylphosphonium bromide.

The starting materials II required for preparing the compounds I are known from the literature [WO-A 95/06033; J.Heterocycl.Chem. 30 (1993), 717; WO-A 97/17328; WO-A 97/24317], or they can be prepared in accordance with the literature quoted.

For example, the α-keto esters IIa (W=—CO—CO—OCH$_3$) can be synthesized as shown in Scheme 1.

Scheme 1:

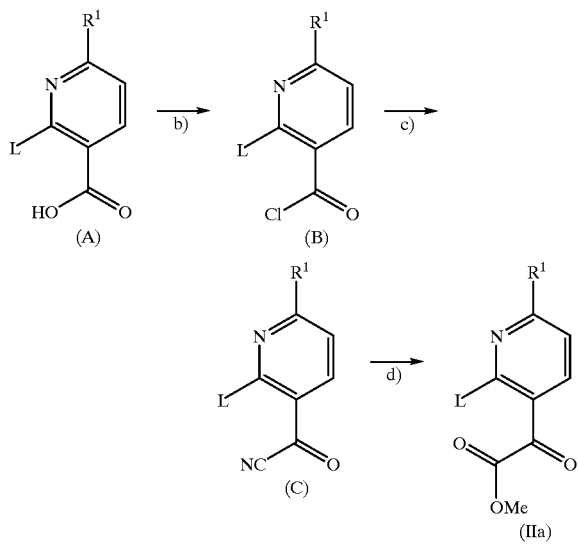

1b) The reaction of the pyridylcarboxylic acid A to give acyl chloride B is carried out in a manner known per se [Houben-Weyl, Supplement Volume 5, p. 59 ff., 225 ff. and 664 ff.; J.Heterocycl.Chem, 30 (1993), 771] using customary chlorinating agents at 0° C.–150° C., preferably at 10° C.–100° C., if appropriate in the presence of an inert organic solvent. Suitable chlorinating agents are all reagents which are customarily used for this purpose, in particular SOCl$_2$, (COCl)$_2$, PCl$_3$, AlCl$_3$ and PCl$_5$. The chlorinating agents are generally employed in excess or, if appropriate, as solvent.

1c) The reaction of the acyl chloride B to give cyanide C is carried out in a manner known per se [WO-A 97/29093] at 0° C.–150° C., preferably at 10° C.–100° C., using an inorganic cyanide in an inert organic solvent, if appropriate as a mixture with water in the presence of a customary phase-transfer catalyst (for example trialkylammonium halides such as tributylammonium chloride or bromide).

Suitable inorganic cyanides are cyanides of metals of the first main group or of the sub-groups of the Periodic Table, for example lithium, sodium, potassium, copper and silver, in particular copper and sodium, and organic cyanides such as trimethylsilyl cyanide.

1d) The reaction of the cyanide C to give α-keto ester IIa is carried out in a manner known per se via a Pinner reaction [WO-A 97/29093] at 0° C.–150° C., preferably at 10° C.–100° C., in the presence of an acid, using methanol as solvent.

The α-keto esters IIaa, which carry a chlorine substitutent in positon 2 of the pyridine ring, can be prepared, as shown diagrammatically in Scheme 2, in only one step starting from 2-chloro- 3-iodo- or 2-fluoro-3-iodopyridines D in a Grignard reaction (cf. Tetrahedron, 52 (1996), 13513–20), or by ortho-metallation of 2-chloro- or 2-fluoropyridines of the formula E and subsequent reaction with methyl α-oxo-α-(1H-imidazol)acetate (J. Heterocyclic Chem., 34 (1997), 789).

Scheme 2:

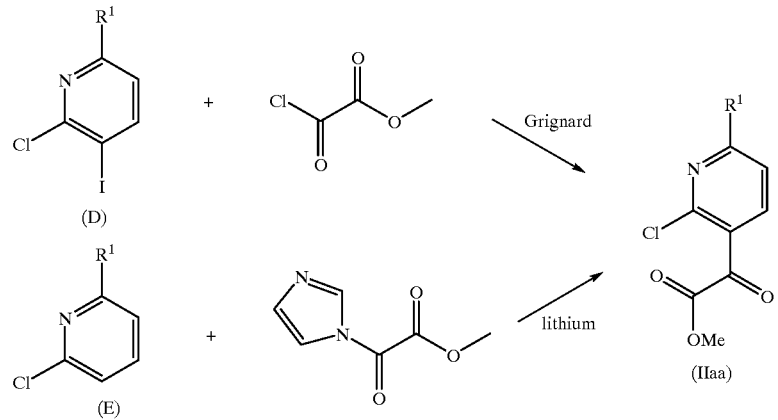

The starting materials III are likewise disclosed in the literature, or they can be prepared by the processes described therein. 3-*Hydroxypyrazoles:* J. Heterocycl. Chem. 30 (1993), page 49; Chem. Ber. 107 (1974), page 1318; Chem. Pharm. Bull. 19 (1971), page 1369; Tetrahedron Lett. 11 (1970), page 875; Chem. Heterocycl. Comp. 5 (1969), page 527; Chem. Ber. 102 (1969), page 3260; Chem. Ber. 109 (1976), page 261; J. Org. Chem. 31 (1966), page 1538; Tetrahedron 43 (1987), page 607; 4-*Hydroxypyrazoles:* CA-A 1 177 081; U.S. Pat. No. 4,621,144; JP-A 60/155, 160].

2-(Pyrazolyloxy)pyridin-3-ylglyoxylic acid methyl ester of the formula Za can be prepared either, as mentioned at the outset, by reaction of the α-keto esters IIa with 3-hydroxypyrazoles III, or from suitable intermediates of the formula Z' in which W is COO—$C_1$–$C_4$-alkyl and $COCH_3$.

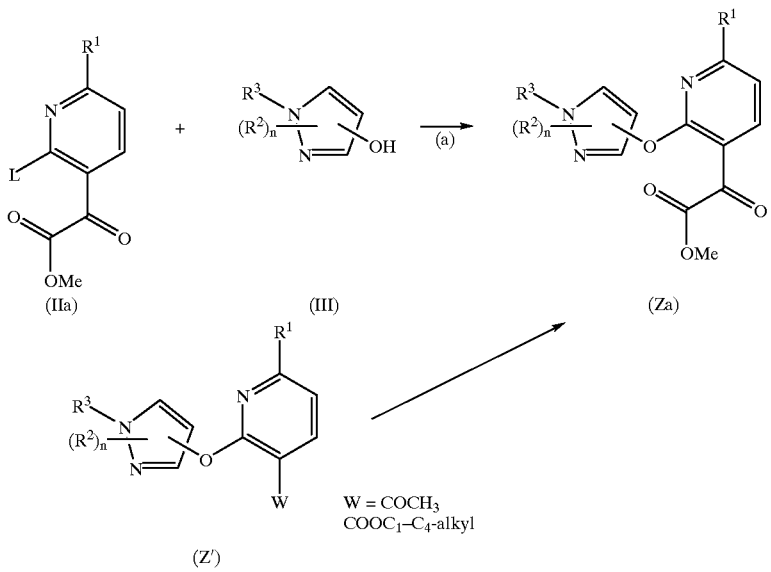

The following synopsis shows which customary reactions are suitable for converting the compounds Z' into the compounds Za:

W=—CO—OR' (R'=$C_1$–$C_4$-alkyl)

Hydrolysis of the —CO—OR'-group to the carboxyl group (cf. Compounds A in Scheme 1);

w=—CO—$CH_3$

Oxidation of the $CH_3$ group (cf.: using potassium permanganate: Houben-Weyl, Volume 4/1b, page 594 ff.; using $SOCl_2$: Tetrahedron Lett. 1976, page 2783 ff.).

The compounds of the formula Za can be converted further into the compounds of the formula I.

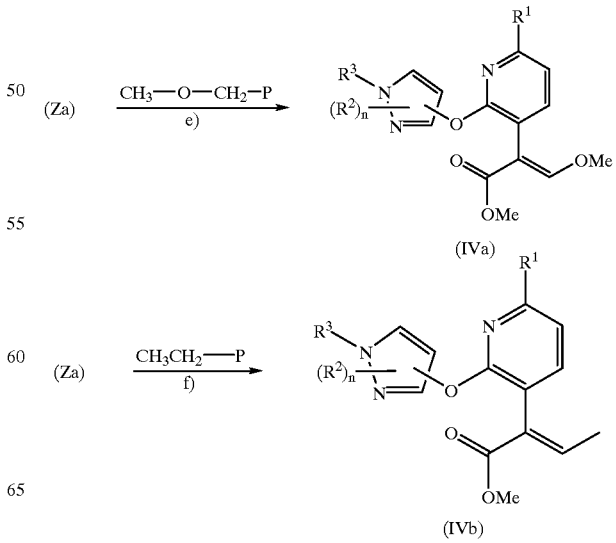

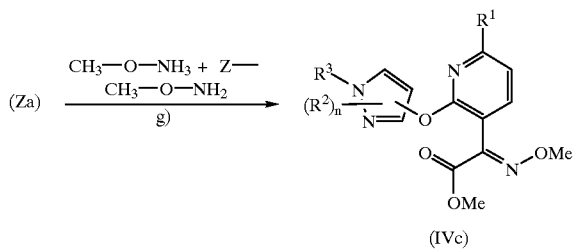

In the formulae IVa and IVb, P is a phosphonium halide radical, in particular $PO(OCH_3)_2$, $PO(OCH_2CH_3)_2$ and $[(C_6H_5)_3P^+Cl^-]$ or a phosphonate suitable for the Wittig or Wittig-Horner reaction.

In the formula IVc, $Z^-$ is the anion of an inorganic acid, especially a halide anion, in particular chloride.

1e) The reaction is carried out in a manner known per se [EP-A 513 580; Tetrahedron (1988), 3727; GB-A 2,172, 595; WO-A 97/29093] via a Wittig or Wittig-Horner reaction at 0° C.–150° C., preferably at 10° C.–100° C. in an inert organic solvent in the presence of a base.

1f) The reaction is carried out in a manner known per se (cf. the literature cited under 1e)) via a Wittig or Wittig-Horner reaction at 0° C.–150° C., preferably at 10° C.–100° C., in an inert organic solvent in the presence of a base.

1g) The reaction is carried out in a manner known per se (EP-A 493 711) at 0° C.–150° C., preferably at 10° C.–100° C., in an inert organic solvent in the presence of a base using O-methylhydroxylamine or a salt thereof (IVc).

2. In another process, the compounds I are obtained, for example, by converting a pyridine derivative of the formula VI in a manner known per se in the presence of a catalyst and using a compound VII into the corresponding pyridine derivative of the formula VIII, and subsequently reacting VIII in the presence of a base with an oxime of the formula IV to give I.

Synthetic route 2:

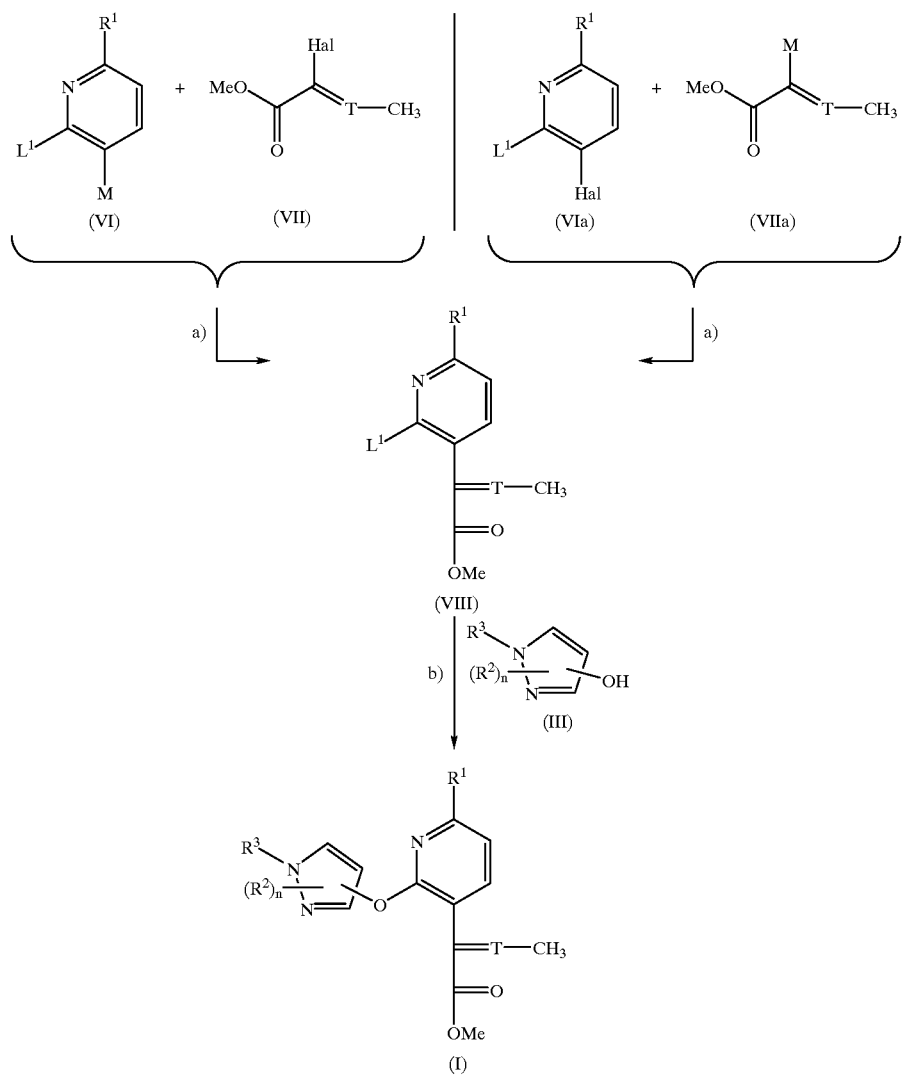

In the formulae VI, VIa and VIII, $L^1$ is a nucleophilically replaceable leaving group, such as aliphatic and aromatic sulfonates and halogens, in particular fluorine and chlorine.

In the formulae VI and VIIa, M is an organometallic radical, for example tributyltin(IV), trimethyltin(IV), zinc(II) chloride (ZnCl) or boron(III) hydroxide [$B(OH)_2$], in particular tributyltin(IV) and boron(III) hydroxide [$B(OH)_2$]. Owing to its high toxicity, the use of trimethyltin(IV) is only preferred under certain conditions.

In the formulae VII, VIIa, VIII and I, T is CHO or NO.

In the formulae VIa and VII, Hal is halogen, in particular bromine or iodine.

In a similar manner, the pyridine derivatives VIII can also be obtained by reacting a halogenated pyridine of the formula VIa with an organometallic compound VIIa.

2a) The reaction of the compound VI or VIa with the carbonyl derivative VII or VIIa is carried out in a manner known per se at 0° C.–150° C., preferably at 10° C.–100° C., in an inert organic solvent, if appropriate in the presence of a cocatalyst such as CuI. If the reaction is carried out with compounds VI or VIIa in which M is $B(OH)_2$, the reaction is carried out in the presence of at least equimolar amounts of a base.

Suitable solvents are aromatic hydrocarbons such as toluene, o-, m- and p-xylene, ethers such as diethyl ether, diisopropyl ether, tert-butyl methyl ether, dimethoxyethane, dioxane, anisole and tetrahydrofuran, and dimethylformamide and dimethylacetamide, water and methanol, particularly preferably N-methylpyrrolidone. It is also possible to employ mixtures of the abovementioned solvents.

Suitable bases for coupling compounds in which M is $B(OH)_2$ are generally inorganic compounds such as alkali metal and alkaline earth metal hydroxides such as lithium hydroxide, sodium hydroxide, potassium hydroxide and calcium hydroxide, alkali metal and alkaline earth metal phosphates such as potassium phosphate, alkali metal and alkaline earth metal oxides such as lithium oxide, sodium oxide, calcium oxide and magnesium oxide, alkali metal and alkaline earth metal carbonates such as lithium carbonate and calcium carbonate and alkali metal bicarbonates such as sodium bicarbonate, and also alkali metal and alkaline earth metal alkoxides such as sodium methoxide, sodium ethoxide, potassium ethoxide, potassium tert-butoxide and dimethoxymagnesium, furthermore organic bases, for example tertiary amines such as trimethylamine, triethylamine, triisopropylethylamine and N-methylpiperidine, pyridine, substituted pyridines such as collidine, lutidine and 4-dimethylaminopyridine and bicyclic amines. Particular preference is given to sodium carbonate, sodium bicarbonate and lithium hydroxide.

The bases are generally employed in equimolar amounts, in excess or, if appropriate, as solvent.

The starting materials are generally reacted with each other in equimolar amounts. In terms of yield, it may be advantageous to employ VI and VIIa in excess, based on VII and VIa, respectively.

The starting materials required for preparing the compounds I are disclosed in the literature [WO-A 95/20569; WO-A 94/24085; Synlett (1) (1995), 32–33; Synlett (4) (1996), 356–357; J.Gen.Chem.USSR 59 (1989), 264–272; Heterocycles 31 (1990), 1543–1548; Tetrahedron 49 (1993), 49–64; J.Chem. Res. Miniprint 11 (1980), 4658–4667], or they can be prepared according to the literature cited.

2b) The reaction of the compound VIII with the hydroxypyrazole III is carried out in a manner known per se at 0° C.–150° C., preferably at 10° C.–100° C., in an inert organic solvent in the presence of a base.

Suitable solvents are alcohols such as methanol, ethanol, n-propanol, isopropanol, n-butanol and tert-butanol, and dimethyl sulfoxide, dimethylformamide and dimethylacetamide, particularly preferably dimethyl sulfoxide, dimethylformamide and dimethylacetamide. It is also possible to use mixtures of the abovementioned solvents.

In general, suitable bases are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal carbonates such as lithium carbonate and calcium carbonate and alkali metal bicarbonates such as sodium bicarbonate, and also alkali metal and alkaline earth metal alkoxides such as sodium methoxide, sodium ethoxide, potassium ethoxide, potassium tert-butoxide and dimethoxymagnesium, furthermore organic bases, for example tertiary amines such as trimethylamine, triethylamine, triisopropylethylamine and N-methylpiperidine, pyridine, substituted pyridines such as collidine, lutidine and 4-dimethylaminopyridine, and also bicyclic amines. Particular preference is given to potassium tert-butoxide, sodium methoxide and potassium carbonate.

In general, the bases are employed in equimolar amounts, in excess or, if appropriate, as solvent.

The starting materials are generally reacted with each other in equimolar amounts. In terms of yield, it may be advantageous to employ an excess of III, based on VIII.

2.1 In accordance with the reaction conditions described above, the compounds I are also particularly preferably obtained by initially converting the pyridine VIa with the hydroxypyrazole III into the corresponding derivative V and subsequently reacting V with VIIa to give I.

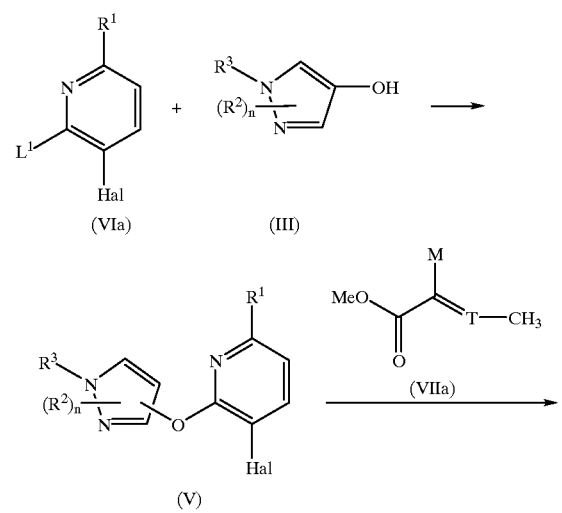

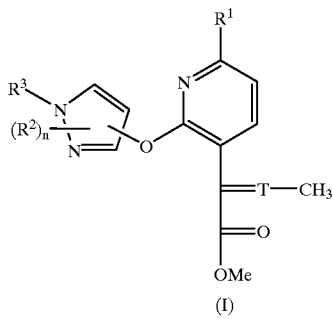

(I)

3. The compounds of the formula I in which Q is a group —C(=NOCH$_3$)CONH(CH$_3$) are advantageously obtained by reacting a compound fo the formula I in which Q=—C(=NOCH$_3$)COOCH$_3$ in a manner known per se with methylamine or its salt.

This reaction is carried out in a manner known per se (EP-A 477 631) at 0° C.–150° C., preferably at 10° C.–100° C., in an inert organic solvent and, if appropriate, in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as aetonitrile and propionitrile, alcohols such as methanol, ethanol, n-propanol, isopropanol, n-butanol and tert-butanol and also dimethyl sulfoxide, dimethylformamide and dimethylacetamide, particularly preferably tetrahydrofuran. It is also possible to employ mixtures of the abovementioned solvents.

In general, suitable bases are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal carbonates such as lithium carbonate and calcium carbonate and alkali metal bicarbonates such as sodium bicarbonate, furthermore organic bases, for example tertiary amines such as trimethylamine, triethylamine, triisopropylethylamine and n-methylpiperidine, pyridine, substituted pyridines, such as collidine, lutidine and 4-dimethylaminopyridine and also bicyclic amines. Particular preference is given to tertiary amines.

In general, the bases are employed in equimolar amounts, in excess or, if appropriate, as solvent.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

Owing to their C=C and C=N double bonds in the group Q, the preparation of the compounds I may yield E/Z isomer mixtures which can be separated into the individual compounds in a customary manner, for example by crystallization or chromatography.

However, if the synthesis yields isomer mixtures, a separation is generally not necessarily required since in some cases the individual isomers can be converted into one another during the preparation for use or upon use (for example under the action of light, acids or bases). Similar conversions may also occur after their use, for example in the treatment of plants in the treated plant or in the harmful fungus or animal pest to be controlled.

In the group Q, with regard to the C=N and C=C double bond, preference is given to the E isomers of the compounds I (configuration based on the (OCH$_3$) or the (CH$_3$) group in relation to the COOCH$_3$ or CONHCH$_3$ group).

The salts of the acid-stable compounds I which contain basic centers, especially basic nitrogen atoms, in particular salts with mineral acids such as sulfuric acid and phosphoric acid or Lewis acids such as zinc chloride also form part of the invention. Usually, the kind of salt does not matter here. For the purposes of the invention, preference is given to those salts which do not damage the plants, areas, materials or spaces to be kept free from harmful fungi or animal pests and which do not negatively affect the action of the compounds I. Particularly important are such salts which are suitable for agricultural purposes.

The salts of the compounds I can be obtained in a manner known per se, in particular by reacting the corresponding compounds I with the abovementioned acids in water or in an inert organic solvent at from –80 to 120, preferably from 0 to 60° C.

In the definitions of the compounds I above, collective terms were used which generally represent the following groups:

halogen: fluorine, chlorine, bromine and iodine;

$C_1-C_4$-alkyl: straight-chain or branched alkyl groups having 1 to 4 carbon atoms, such as methyl, ethyl, propyl, 1-methylethyl, butyl, 1-methylpropyl, 2-methylpropyl, 1,1-dimethylethyl;

$C_1-C_4$-haloalkyl: straight-chain or branched alkyl groups having 1 to 4 carbon atoms, it being possible for some or all of the hydrogen atoms in these groups to be replaced by halogen atoms as mentioned above, for example $C_1-C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_4$-alkoxy and the $C_1-C_4$-alkoxy moiety of $C_1-C_4$-alkoxycarbonyl: straight-chain or branched alkyl groups having 1 to 4 carbon atoms as mentioned above, which are attached to the skeleton via an oxygen atom (—O—), for example $C_1-C_4$-alkoxy such as methyloxy, ethyloxy, propyloxy, 1-methylethyloxy, butyloxy, 1-methylpropyloxy, 2-methylpropyloxy, 1,1-dimethylethyloxy;

$C_1-C_2$-haloalkoxy: straight-chain alkyl groups having 1 to 2 carbon atoms, it being possible for some or all of the hydrogen atoms in these groups to be replaced by halogen atoms as mentioned above, these groups being attached to the skeleton via an oxygen atom, for example chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy.

The term "partially or fully halogenated" is meant to express that in the groups characterized in this manner the hydrogen atoms may be partially or fully replaced by identical or different halogen atoms as mentioned above.

In terms of their activity for controlling harmful fungi and animal pests, preference is given to compounds of the formulae Ia and Ib

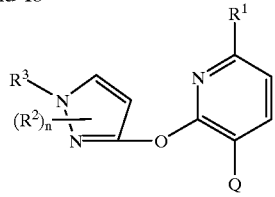

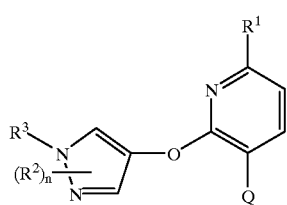

and salts thereof in which the substituents and the index n, in each case alone or in combination, have the following meanings:

n is 0 or 1;

$R^1$ is hydrogen, halogen, halomethyl;

$R^2$ is chlorine, bromine, methyl or trifluoromethyl:

$R^3$ is phenyl, pyridyl and pyrimidyl, where the phenyl, pyridyl and pyrimidyl radical may carry one or, independently of one another, two or three of the following substituents: halogen, cyano, $C_1$–$C_4$-alkyl, $C_1$–$C_2$-haloalkyl, $C_1$–$C_4$-alkoxy, $C_1$–$C_2$-haloalkoxy or $C_1$–$C_4$-alkoxycarbonyl.

Q is —C(=CHCH$_3$)—COOCH$_3$,—C(=CHOCH$_3$)—COOCH$_3$,—C(=NOCH$_3$)—COOCH$_3$ or —C(=NOCH$_3$)—CONH(CH$_3$);

Particular preference is given to compounds I and salts thereof in which the substituents and the index n have the following meanings:

n is 0 or 1;

Q is —C(=CHOCH$_3$)—COOCH$_3$, —C(=NOCH$_3$)—CONH(CH$_3$);

$R^1$ is hydrogen, halogen, halomethyl;

$R^2$ is chlorine, bromine, methyl or trifluoromethyl:

$R^3$ is phenyl, where the phenyl ring may carry one or, independently of one another, two or three of the following substituents: halogen, cyano, $C_1$–$C_4$-alkyl, $C_1$–$C_2$-haloalkyl, $C_1$–$C_4$-alkoxy, $C_1$–$C_2$-haloalkoxy or $C_1$–$C_4$-alkoxycarbonyl.

Preference is also given to the compounds of the formula I and salts thereof in which the pyrazolyloxy group has one of the following meanings:

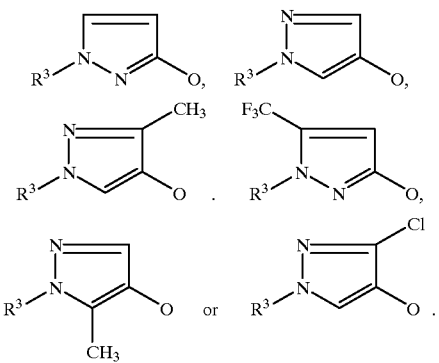

In terms of their biological activity, very particular preference is given to the compounds compiled in the following tables, where in the various groups Q the double bonds adjacent to the central pyridine ring are in each case in the E configuration.

Table 1
Compounds of the formula IA,

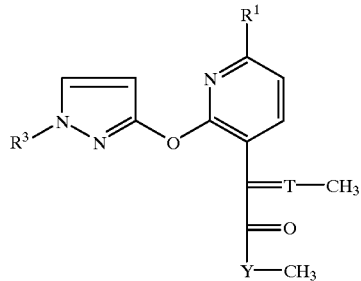

Where T is N—O and Y is O, while the meanings of the radicals $R^1$ and $R^3$ correspond for each compound to a row of Table A.

Table 2
Compounds of the formula IA where T is N—O and Y is NH, while the meanings of the radicals $R^1$ and $R^3$ correspond for each compound to a row of Table A.

Table 3
Compounds of the formula IA where T is CH—O and Y is OH, while the meanings of the radicals $R^1$ and $R^3$ correspond for each compound to a row of Table A.

Table 4
Compounds of the formula IA where T is CH and Y is O, while the meanings of the radicals $R^1$ and $R^3$ correspond for each compound to a row of Table A.

Table 5
Compounds of the formula IB,

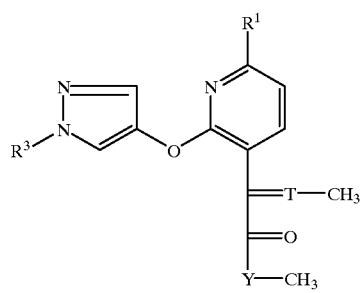

where T is N—O and Y is O, while the meanings of the radicals $R^1$ and $R^3$ correspond for each compound to a row of Table A.

Table 6
Compounds of the formula IB where T is N—O and Y is NH, while the meanings of the radicals $R^1$ and $R^3$ correspond for each compound to a row of Table A.

Table 7
Compounds of the formula IB where T is CH—O and Y is O, while the meanings of the radicals $R^1$ and $R^3$ correspond for each compound to a row of Table A.

Table 8
Compounds of the formula IB where T is CH and Y is O, while the meanings of the radicals $R^1$ and $R^3$ correspond for each compound to a row of Table A.

Table 9
Compounds of the formula IC,

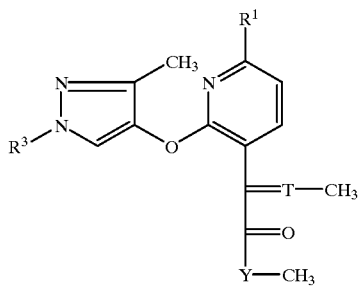

(IC)

where T is N—O and Y is O, while the meanings of the radicals $R^1$ and $R^3$ correspond for each compound to a row of Table A.

Table 10
Compounds of the formula IC, where T is N—O and Y is NH, while the meanings of the radicals $R^1$ and $R^3$ correspond for each compound to a row of Table A.

Table 11
Compounds of the formula IC, where T is CH—O and Y is O, while the meanings of the radicals $R^1$ and $R^3$ correspond for each compound to a row of Table A.

Table 12
Compounds of the formula IC, where T is CH and Y is O, while the meanings of the radicals $R^1$ and $R^3$ correspond for each compound to a row of Table A.

Table 13
Compounds of the formula ID,

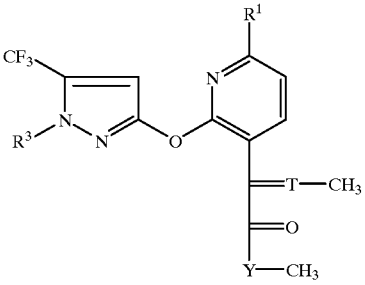

(ID)

where T is N—O and Y is O, while the meanings of the radicals $R^1$ and $R^3$ correspond for each compound to a row of Table A.

Table 14
Compounds of the formula ID, where T is N—O and Y is NH, while the meanings of the radicals $R^1$ and $R^3$ correspond for each compound to a row of Table A.

Table 15
Compounds of the formula ID, where T is CH—O and Y is O, while the meanings of the radicals $R^1$ and $R^3$ correspond for each compound to a row of Table A.

Table 16
Compounds of the formula ID, where T is CH and Y is O, while the meanings of the radicals $R^1$ and $R^3$ correspond for each compound to a row of Table A.

Table 17
Compounds of the formula IE,

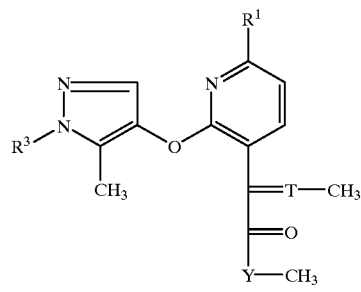

(IE)

where T is N—O and Y is O, while the meanings of the radicals $R^1$ and $R^3$ correspond for each compound to a row of Table A.

Table 18
Compounds of the formula IE, where T is N—O and Y is NH, while the meanings of the radicals $R^1$ and $R^3$ correspond for each compound to a row of Table A.

Table 19
Compounds of the formula IE, where T is CH—O and Y is O, while the meanings of the radicals $R^1$ and $R^3$ correspond for each compound to a row of Table A.

Table 20
Compounds of the formula IE, where T is CH and Y is O, while the meanings of the radicals $R^1$ and $R^3$ correspond for each compound to a row of Table A.

Table 21
Compounds of the formula IF,

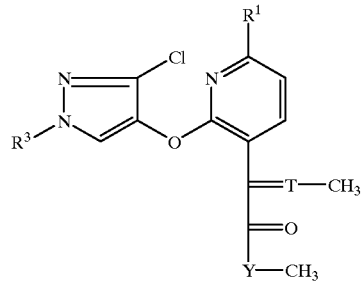

(IF)

where T is N—O and Y is O, while the meanings of the radicals $R^1$ and $R^3$ correspond for each compound to a row of Table A.

Table 22
Compounds of the formula IF, where T is N—O and Y is NH, while the meanings of the radicals $R^1$ and $R^3$ correspond for each compound to a row of Table A.

Table 23
Compounds of the formula IF, where T is CH—O and Y is O, while the meanings of the radicals $R^1$ and $R^3$ correspond for each compound to a row of Table A.

Table 24

Compounds of the formula IF, where T is CH and Y is O, while the meaning of the radicals $R^1$ and $R^3$ correspond for each compound to a row of Table A.

TABLE A

| No. | $R^1$ | $R^3$ |
|---|---|---|
| A.1 | H | $C_6H_5$ |
| A.2 | Cl | $C_6H_5$ |
| A.3 | Br | $C_6H_5$ |
| A.4 | F | $C_6H_5$ |
| A.5 | $CCl_3$ | $C_6H_5$ |
| A.6 | $CF_3$ | $C_6H_5$ |
| A.7 | H | 2-F—$C_6H_4$ |
| A.8 | H | 3-F—$C_6H_4$ |
| A.9 | H | 4-F—$C_6H_4$ |
| A.10 | Cl | 4-F—$C_6H_4$ |
| A.11 | Br | 4-F—$C_6H_4$ |
| A.12 | F | 4-F—$C_6H_4$ |
| A.13 | $CCl_3$ | 4-F—$C_6H_4$ |
| A.14 | $CF_3$ | 4-F—$C_6H_4$ |
| A.15 | H | 2,3-$F_2$—$C_6H_3$ |
| A.16 | H | 2,4-$F_2$—$C_6H_3$ |
| A.17 | Cl | 2,4-$F_2$—$C_6H_3$ |
| A.18 | Br | 2,4-$F_2$—$C_6H_3$ |
| A.19 | F | 2,4-$F_2$—$C_6H_3$ |
| A.20 | $CCl_3$ | 2,4-$F_2$—$C_6H_3$ |
| A.21 | $CF_3$ | 2,4-$F_2$—$C_6H_3$ |
| A.22 | H | 2,5-$F_2$—$C_6H_3$ |
| A.23 | H | 2,6-$F_2$—$C_6H_3$ |
| A.24 | H | 3,4-$F_2$—$C_6H_3$ |
| A.25 | H | 3,5-$F_2$—$C_6H_3$ |
| A.26 | Cl | 3,5-$F_2$—$C_6H_3$ |
| A.27 | Br | 3,5-$F_2$—$C_6H_3$ |
| A.28 | F | 3,5-$F_2$—$C_6H_3$ |
| A.29 | $CCl_3$ | 3,5-$F_2$—$C_6H_3$ |
| A.30 | $CF_3$ | 3,5-$F_2$—$C_6H_3$ |
| A.31 | H | 2-Cl—$C_6H_4$ |
| A.32 | H | 3-Cl—$C_6H_4$ |
| A.33 | H | 4-Cl—$C_6H_4$ |
| A.34 | Cl | 4-Cl—$C_6H_4$ |
| A.35 | Br | 4-Cl—$C_6H_4$ |
| A.36 | F | 4-Cl—$C_6H_4$ |
| A.37 | $CCl_3$ | 4-Cl—$C_6H_4$ |
| A.38 | $CF_3$ | 4-Cl—$C_6H_4$ |
| A.39 | H | 2,3-$Cl_2$—$C_6H_3$ |
| A.40 | H | 2,4-$Cl_2$—$C_6H_3$ |
| A.41 | Cl | 2,4-$Cl_2$—$C_6H_3$ |
| A.42 | Br | 2,4-$Cl_2$—$C_6H_3$ |
| A.43 | F | 2,4-$Cl_2$—$C_6H_3$ |
| A.44 | $CCl_3$ | 2,4-$Cl_2$—$C_6H_3$ |
| A.45 | $CF_3$ | 2,4-$Cl_2$—$C_6H_3$ |
| A.46 | H | 2,5-$Cl_2$—$C_6H_3$ |
| A.47 | H | 2,6-$Cl_2$—$C_6H_3$ |
| A.48 | H | 3,4-$Cl_2$—$C_6H_3$ |
| A.49 | H | 3,5-$Cl_2$—$C_6H_3$ |
| A.50 | Cl | 3,5-$Cl_2$—$C_6H_3$ |
| A.51 | Br | 3,5-$Cl_2$—$C_6H_3$ |
| A.52 | F | 3,5-$Cl_2$—$C_6H_3$ |
| A.53 | $CCl_3$ | 3,5-$Cl_2$—$C_6H_3$ |
| A.54 | $CF_3$ | 3,5-$Cl_2$—$C_6H_3$ |
| A.55 | H | 2,3,4-$Cl_3$—$C_6H_2$ |
| A.56 | H | 2,3,5-$Cl_3$—$C_6H_2$ |
| A.57 | H | 2,3,6-$Cl_3$—$C_6H_2$ |
| A.58 | H | 2,4,5-$Cl_3$—$C_6H_2$ |
| A.59 | H | 2,4,6-$Cl_3$—$C_6H_2$ |
| A.60 | H | 3,4,5-$Cl_3$—$C_6H_2$ |
| A.61 | H | 2-Br—$C_6H_4$ |
| A.62 | H | 3-Br—$C_6H_4$ |
| A.63 | H | 4-Br—$C_6H_4$ |
| A.64 | H | 2,4-$Br_2$—$C_6H_3$ |
| A.65 | H | 2-Br, 4-F—$C_6H_3$ |
| A.66 | H | 2-Br, 4-Cl—$C_6H_3$ |
| A.67 | H | 2-F, 4-Cl—$C_6H_3$ |
| A.68 | H | 3-F, 4-Cl—$C_6H_3$ |
| A.69 | H | 3-Cl, 5-F—$C_6H_3$ |
| A.70 | H | 2-Cl, 4-F—$C_6H_3$ |
| A.71 | H | 2-CN—$C_6H_4$ |
| A.72 | H | 3-CN—$C_6H_4$ |
| A.73 | H | 4-CN—$C_6H_4$ |
| A.74 | H | 3-CN, 4-Cl—$C_6H_3$ |
| A.75 | H | 2-$CH_3$—$C_6H_4$ |
| A.76 | H | 3-$CH_3$—$C_6H_4$ |
| A.77 | H | 4-$CH_3$—$C_6H_4$ |
| A.78 | Cl | 4-$CH_3$—$C_6H_4$ |
| A.79 | Br | 4-$CH_3$—$C_6H_4$ |
| A.80 | F | 4-$CH_3$—$C_6H_4$ |
| A.81 | $CCl_3$ | 4-$CH_3$—$C_6H_4$ |
| A.82 | $CF_3$ | 4-$CH_3$—$C_6H_4$ |
| A.83 | H | 2,4-$(CH_3)_2$—$C_6H_3$ |
| A.84 | Cl | 2,4-$(CH_3)_2$—$C_6H_3$ |
| A.85 | Br | 2,4-$(CH_3)_2$—$C_6H_3$ |
| A.86 | F | 2,4-$(CH_3)_2$—$C_6H_3$ |
| A.87 | $CCl_3$ | 2,4-$(CH_3)_2$—$C_6H_3$ |
| A.88 | $CF_3$ | 2,4-$(CH_3)_2$—$C_6H_3$ |
| A.89 | H | 2,5-$(CH_3)_2$—$C_6H_3$ |
| A.90 | H | 2,5-$(CH_3)_2$—$C_6H_3$ |
| A.91 | H | 2,6-$(CH_3)_2$—$C_6H_3$ |
| A.92 | H | 3,4-$(CH_3)_2$—$C_6H_3$ |
| A.93 | H | 3,5-$(CH_3)_2$—$C_6H_3$ |
| A.94 | H | 2,4,6-$(CH_3)_3$—$C_6H_2$ |
| A.95 | H | 3,4,5-$(CH_3)_3$—$C_6H_2$ |
| A.96 | H | 2-$CH_3$, 4-Cl—$C_6H_3$ |
| A.97 | H | 2-Cl, 4-$CH_3$—$C_6H_3$ |
| A.98 | H | 3-$CH_3$, 4-Cl—$C_6H_3$ |
| A.99 | H | 3-Cl, 5-$CH_3$—$C_6H_3$ |
| A.100 | H | 2-CN, 4-$CH_3$—$C_6H_3$ |
| A.101 | H | 2-$CH_3$, 4-CN—$C_6H_3$ |
| A.102 | H | 4-$(C_2H_5)$—$C_6H_4$ |
| A.103 | H | 4-[$C(CH_3)_3$]—$C_6H_4$ |
| A.104 | H | 2-$CF_3$—$C_6H_4$ |
| A.105 | H | 3-$CF_3$—$C_6H_4$ |
| A.106 | H | 4-$CF_3$—$C_6H_4$ |
| A.107 | H | 3,5-$(CF_3)_2$—$C_6H_3$ |
| A.108 | H | 2-Cl, 4-$CF_3$—$C_6H_3$ |
| A.109 | H | 2-$OCH_3$—$C_6H_4$ |
| A.110 | H | 3-$OCH_3$—$C_6H_4$ |
| A.111 | H | 4-$OCH_3$—$C_6H_4$ |
| A.112 | H | 2,4-$(OCH_3)_2$—$C_6H_3$ |
| A.113 | H | 3,4-$(OCH_3)_2$—$C_6H_3$ |
| A.114 | H | 2,5-$(OCH_3)_2$—$C_6H_3$ |
| A.115 | H | 3,5-$(OCH_3)_2$—$C_6H_3$ |
| A.116 | H | 3,4,5-$(OCH_3)_3$—$C_6H_2$ |
| A.117 | H | 2-$CH_3$, 4-$OCH_3$—$C_6H_3$ |
| A.118 | H | 2-Cl, 4-$OCH_3$—$C_6H_3$ |
| A.119 | H | 4-$OCF_3$—$C_6H_4$ |
| A.120 | H | 2-$OCHF_2$—$C_6H_4$ |
| A.121 | H | 3-$OCHF_2$—$C_6H_4$ |
| A.122 | H | 4-$OCHF_2$—$C_6H_4$ |
| A.123 | H | 4-$(OCF_2CHF_2)$—$C_6H_4$ |
| A.124 | H | 2-F, 4-$OCHF_2$—$C_6H_3$ |
| A.125 | H | 4-$(OCH_2CH_3)$—$C_6H_4$ |
| A.126 | H | 4-[$OC(CH_3)_3$]—$C_6H_4$ |
| A.127 | H | 3-$(CO_2CH_3)$—$C_6H_4$ |
| A.128 | H | 4-$(CO_2CH_3)$—$C_6H_4$ |
| A.129 | H | 4-[$CO_2C(CH_3)_3$]—$C_6H_4$ |
| A.130 | H | pyridin-2-yl |
| A.131 | H | 5-Cl-pyridin-2-yl |
| A.132 | H | 3,5-$Cl_2$-pyridin-2-yl |
| A.133 | H | 5-$CF_3$-pyridin-2-yl |
| A.134 | H | 3-Cl, 5-$CF_3$-pyridin-2-yl |
| A.135 | H | 3-Cl-pyridin-2-yl |
| A.136 | H | 4-Cl-pyrimidin-6-yl |
| A.137 | H | 6-$CF_3$-pyrimidin-4-yl |

The compounds I are suitable as fungicides. They have excellent activity against a broad spectrum of phytopathogenic fungi, in particular from the class of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soya, coffee, sugar cane, grape vines, fruit species, ornamentals and vegetable species such as cucumbers, beans, tomatoes, potatoes and cucurbits, and also in the seeds of these plants.

Specifically, they are suitable for controlling the following plant diseases:

*Alternaria* species in vegetables and fruit,

*Botrytis cinerea* (gray mold) in strawberries, vegetables, ornamentals and grape vines,

*Cercospora arachidicola* in groundnuts,

*Erysiphe cichoracearum* and *Sphaerotheca fuliginea* in cucurbits,

*Erysiphe graminis* (powdery mildew) in cereals,

Fusarium and Verticillium species in a variety of plants,

Helminthosporium species in cereals,

Mycosphaerella species in bananas and groundnuts,

*Phytophthora infestans* in potatoes and tomatoes,

*Plasmopara viticola* in grape vines,

*Podosphaera leucotricha* in apples,

*Pseudocercosporella herpotrichoides* in wheat and barley,

Pseudoperonospora species in hops and cucumbers,

Puccinia species in cereals,

*Pyricularia oryzae* in rice,

Rhizoctonia species in cotton, rice and lawns,

*Septoria nodorum* in wheat,

*Uncinula necator* in grape vines,

Ustilago species in cereals and sugar cane, and

*Venturia inaequalis* (scab) in apples and pears.

The compounds I are also suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application is carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds of the formula I are also suitable for the efficient control of animal pests from the class of the insects, arachnids and nematodes. They can be used for controlling animal pests in crop protection and in the sectors of hygiene, protection of stored products and in the veterinary sector. They are particularly suitable for controlling the following animal pests:

Insects from the order of the lepidopterons (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Helioverpa armigera, Helioverpa virescens, Helioverpa zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), eg. *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, phyllophaga sp., Phyllopertha horticola, Phyllotreta nemorum, Phyllotreta striolata, Popillia japonica, Sitona lineatus* and *Sitophilus granaria,* dipterons (Diptera), eg. *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterons (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta*, heteropterons (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, homopterons (Homoptera), eg. *Acyrthosiphon onobrychis, Adelges laricis, Aphidula nasturtii, Aphis fabae, Aphis gassypii, Aphis pomi, Aphis sambuci, Brachycaudus cardui, Brevicoryne brassicae, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphum rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii*, termites (Isoptera), eg. *Calotermes flavicollis, Leucotermes flavipes, Reticulitermes lucifugus* and *Termes natalensis*, orthopterons (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, Arachnoidea such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae*, nematodes such as root ball nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii*, stem and leaf nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

For controlling animal pests outdoors, the application rate of active compound is from 0.1 to 2.0, preferably 0.2 to 1.0, kg/ha.

The compounds I can be converted into the customary formulations, eg. solutions, emulsions, suspensions, dusts, powders, pastes and granules. The use form depends on the specific intended use; in any case, it should ensure fine and uniform distribution of the compound according to the invention.

The formulations are prepared in a known manner, eg. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolin, clays, talc, chalk) and ground synthetic minerals (eg. finely divided silica, silicates); emulsifiers such as nonionic and anionic emulsifiers (eg. polyoxyethylene fatty alcohol ethers, alkylsulfonates and arylsulfonates), and dispersants such as ligninsulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Suitable for preparing directly sprayable solutions, emulsions, pastes or oil dispersions are petroleum fractions having medium to high boiling points, such as kerosine or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or jointly grinding the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

The active compounds can be applied as such, in the form of their formulations or in the application forms prepared therefrom, for is example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))

benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-1-(2,2,2-trichloroethyl)formamide, 1-(3,4-dichloroanilino)-1-formylamino-2,2,2-trichloroethane, amines, such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl] piperidine, 8-(1,1-dimethylethyl)-N-ethyl-N-propyl-1,4-dioxaspiro[4.5] decane-2-methaneamine;

azoles such as 1-[2-(2,4-dichloro- phenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxy ethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-yl-methyl]-1H-1,2,4-triazole, 1-[2-(2,4-dichlorophenyl)pentyl]-1H-1,2,4-triazole, 2,4'-difluoro-α-(1H-1,2,4-triazolyl-1-methyl)benzhydryl alcohol, 1-((bis(4-fluorophenyl)methylsilyl)methyl)-1H-1,2,4-triazole, 1-[2RS,4RS;2RS,4SR-4-bromo-2-[2,4-dichlorophenyl) tetrahydrofuryl]-1H-1,2,4-triazole, 2-(4-chlorophenyl)-3-cyclopropyl-1-(1H-1,2,4-triazol-1-yl)butan-2-ol, (+)-4-chloro-4-[4-methyl-2-(1H-1,2,4-triazol-1-ylmethyl)-1,3-dioxolan-2-yl]phenyl 4-chlorophenyl ether, (E)-(R,S)-1-(2,4-dichlorophenyl)-4,4-dimethyl-2-(1H-1,2,4-triazol-1-yl)pent-1-en-3-ol, 4-(4-chlorophenyl)-2-phenyl-2-(1H-1,2,4-triazolylmethyl)butyronitrile, 3-(2,4-dichlorophenyl)-6-fluoro-2-(1H-1,2,4-triazol-1-yl)-quinazolin-4(3H)-one,(R,S)-2-(2,4-dichlorophenyl)-1H-1,2,4-triazol-1-yl)-hexan -2-ol, (1RS,5RS;1RS,5SR)-5-(4-chlorobenzyl)-2,2-dimethyl-1-(1H-1,2,4-triazol-1-ylmethyl)cyclopentanol, (R,S-1-(4-chlorophenyl) 4,4-dimethyl-3-(1H-1,2,4-triazol-1-ylmethyl)pentan-3-ol, (+)-2-(2,4-dichlorophenyl)-3-(1H-1,2,4-triazolyl)propyl 1,1,2,2-tetrafluoroethyl ether, (E)-1-[1-[[4-chloro-2-(trifluoromethyl)phenyl] imino]-2-propoxyethyl]-1H-imidazole, 2-(4-chlorophenyl)-2-(1H-1,2,4-triazol-1-ylmethyl) hexanenitrile;

α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene;

strobilurins, such as methyl E-methoximino-[α-(o-tolyloxy)-o-tolyl]acetate, methyl E-2-{2-[6-(2-cyanophenoxy) pyridimin-4-yloxy]-phenyl}-3-methoxyacrylate, N-methyl E-methoxyimino-(α-(2-phenoxyphenyl))acetamide, methyl-E-methoxyimino-(α-(2,5-dimethylphenoxy)-o-tolyl]acetamide;

anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline;

phenylpyrroles, such as 4-(2,2-difluoro-1,3-benzodioxol-4-yl)pyrrole-3-carbonitrile;

cinnamamides, such as 3-(4-chlorophenyl)-3-(3,4-dimethoxyphenyl)acryloylmorphine;

and a variety of fungicides, such as dodecylguanidine acetate, 3-[3-(3,5-dimethyl-2-oxycyclohexyl)-2-hydroxyethyl]glutarimide, N-methyl-, N-ethyl-(4-trifluoromethyl-2-[31,4,-dimethoxyphenyl]benzamide, hexachlorobenzene, methyl N-(2,6-dimethylphenyl)-N-(2-furoyl)-DL-alaninate, DL-N-(2,6-dimethylphenyl)-N-(2'-methoxy-acetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl carbamoylhydantoin, N-(3,5-dichlorophenyl)-1,2-dimethylcyclopropane-1,2-dicarboximide, 2-cyano-[N-(ethylaminocarbonyl)-2-methoximino]acetamide, N-(3-chloro-2,6-dinitro-4-trifluoromethylphenyl)-5-trifluoro-methyl-3-chloro-2-aminopyridine.

SYNTHESIS EXAMPLES

The procedures given in the synthesis examples below were used to obtain further compounds I by appropriate modification of the starting materials. The compounds obtained in this manner are listed in the Table B which follows, together with physical data.

1. Preparation of methyl methoxyimino-[2-(1-(4-chlorophenyl)-3-pyrazolyloxy)pyridin-3-yl]acetate (Compound I.1 of Table B)

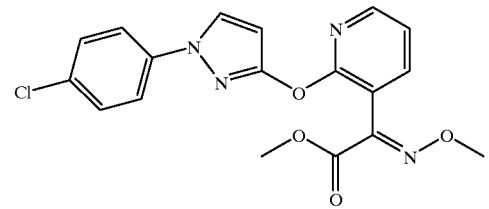

1a. Methyl [2-(1-(4-chlorophenyl)-3-pyrazolyloxy)pyridin-3-yl]glyoxylate

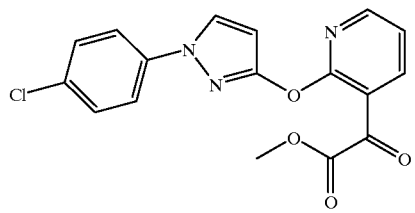

At 60° C., 4.7 g (42 mmol) of potassium tert-butoxide were added a little at a time to a solution of 7.4 g (38.1 mmol) of 1-(4-chlorophenyl)-3-hydroxypyrazole in 15 ml of tert-butanol. The mixture was stirred at this temperature for 1 hour and the solvent was then removed under reduced pressure. The residue was dissolved in 25 ml of abs. dimethyl sulfoxide, and a solution of 8.0 g (38.1 mmol) of methyl (2-chloropyridin-3-yl)glyoxylate in 10 ml of abs. dimethyl sulfoxide was then added at such a rate that the temperature did not exceed 30° C. After 30 minutes at room temperature, 50 ml of 0.5 N HCl were added and the reaction mixture was extracted repeatedly with ethyl acetate. The combined organic phases were washed with water and dried over sodium sulfate. The solvent was subsequently removed under reduced pressure. The resulting residue was purified by silica gel column chromatography using cyclohexane/ethyl acetate (10:1) as eluant. 5.5 g (40%) of the title compound were obtained as a clear oil.

1.b Methyl methoxyimino-[2-(1-(4-chlorophenyl)-3-pyrazolyloxy)pyridin-3-yl]acetate A mixture of 2.7 g (7.3 mmol) of methyl [2-(1-(4-chlorophenyl)-3-pyrazolyloxy)pyridin-3-yl]glyoxylate (Example 1a.), 1.16 g of pyridine and 25 ml of methanol were admixed with 0.67 g (8.0 mmol) of O-methylhydroxylamine hydrochloride, and the mixture was stirred at room temperature for 1.5 hours. The resulting precipitate was separated off and washed with ice-cold methanol. The residue was freed from the solvent under reduced pressure. 1.2 g (42%) of the title compound were obtained as a white solid.

2. N-methyl-methoxyimino-[2-(1-(4-chlorophenyl)-3-pyrazolyloxy)pyridin-3-yl]acetamide (Compound I.2 of Table B)

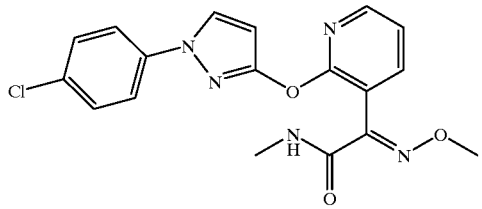

A mixture of 0.65 g (1.7 mmol) of methyl methoxyimino-[2-(1-(4-chlorophenyl)-3-pyrazolyloxy)pyridin-3-yl]acetate (Example 1.b) and 3.2 g of 40% strength aqueous methylamine solution in 2 ml of tetrahydrofuran were heated under reflux for 0.5 hours. The reaction mixture was freed from the solvent under reduced pressure. The residue was stirred with pentane/water, and the solid was separated off, washed with water and dried under reduced pressure. 0.55 g (84%) of the title compound was obtained as a white solid.

3. Methyl methoxy-[2-(1-(4-chlorophenyl)-3-pyrazolyloxy)pyridin-3-yl]acrylate (Comp. I.3 of Table B)

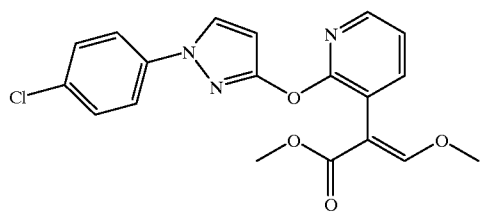

At room temperature, a mixture of 1.86 g (5.4 mmol) of methoxymethyltriphenylphosphonium chloride and 0.98 g (5.4 mmol) of sodium methoxide solution (30% strength in methanol) in 15 ml of dimethylformamide was stirred for 10 minutes. Subsequently, the reaction mixture was admixed with 1.0 g (2.72 mmol) of methyl [2-(1-(4-chlorophenyl)-3-pyrazolyloxy)pyridin-3-yl]glyoxylate (Example 1a.) dissolved in 5 ml of dimethylformamide. The reaction mixture was stirred at room temperature for 2 hours and then hydrolyzed with 20 ml of water. The aqueous phase was subsequently extracted with methyl tert-butyl ether. The combined organic phases were dried over sodium sulfate and the solvent was subsequently removed under reduced pressure. 0.6 g (57%) of the title compound was obtained in the form of a yellow solid.

TABLE B

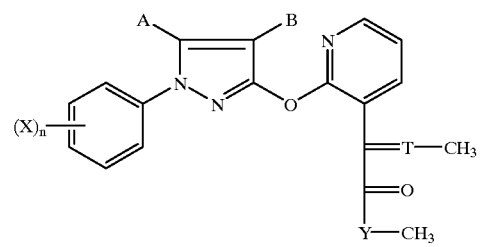

| No. | (X)$_n$ | A | B | Y | T | Physical data (MP., $^1$H NMR; CDCl$_3$ [ppm]) |
|---|---|---|---|---|---|---|
| I.1 | 4-Cl | H | H | O | N—O | 131° C. |
| I.2 | 4-Cl | H | H | NH | N—O | 193° C. |
| I.3 | 4-Cl | H | H | O | CH—O | 120° C. |
| I.4 | 4-OMe | H | H | O | N—O | 102° C. |
| I.5 | 4-OMe | H | H | NH | N—O | 136–139° C. |
| I.6 | 4-OMe | H | H | O | CH—O | 3.70(s, 3H, OCH$_3$), 3.82(s, 3H, OCH$_3$), 3.86(s, 3H, OCH$_3$), 6.18(s, 1H, CH), 6.9(s, 1H, CH), 6.96(s, 1H, CH), 7.08(m, 1H, CH), 7.5–7.64(m, 4H, CH), 7.8(s, 1H, CH), 8.14(m, 1H, CH) |
| I.7 | 2,4-difluoro | H | H | O | N—O | 98° C. |
| I.8 | 2,4-difluoro | H | H | NH | N—O | 2.9(d, 3H, NCH$_3$), 4.0(s, 3H, OCH$_3$) 6.26(s, 1H, CH), 6.8(d, 1H, NH), 6.9–7.04(m, 2H, CH), 7.15(m, 1H, CH), 7.7(d, 1H, CH), 7.8–7.92(m, 2H, CH), 8.25(1H) |

TABLE B-continued

[Structure: pyrazole with substituents A, B, (X)n-phenyl, linked via O to pyridine with T-CH3, =O, Y-CH3 groups]

| No. | (X)$_n$ | A | B | Y | T | Physical data (MP., $^1$H NMR; CDCl$_3$ [ppm]) |
|---|---|---|---|---|---|---|
| I.9 | 2,4-difluoro | H | H | O | CH—O | 3.7(s, 3H, OCH$_3$), 3.9(s, 3H, OCH$_3$), 6.24(s, 1H, CH), 6.95(m, 2H, CH), 7.2(m, 1H, CH), 7.6(m, 2H, CH), 7.86(m, 2H, CH), 8.15(m, 1H, CH) |
| I.10 | 4-Cl | CF$_3$ | H | O | N—O | 3.91(s, 3H, OCH$_3$), 4.10(s, 3H, OCH$_3$), 6.68(s, 1H, CH), 7.18(m, 1H, CH), 7.40–7.50(m, 4H, CH), 7.75(d, 1H, CH), 8.27(d, 1H, CH) |
| I.11 | 4-Cl | CF$_3$ | H | NH | N—O | 2.95(d, 3H, NCH$_3$), 3.98(s, 3H, OCH$_3$), 6.75(s, 1H, CH), 6.81(q, 1H, NH), 7.18(m, 1H, CH), 7.42–7.51(m, 4H, CH), 7.64(d, 1H, CH), 8.26(d, 1H, CH) |
| I.12 | 4-Cl | CF$_3$ | H | O | CH—O | 3.72(s, 3H, OCH$_3$), 3.88(s, 3H, OCH$_3$), 6.68(s, 1H, CH), 7.12(m, 1H, CH), 7.41–7.50(m, 4H, CH), 7.60(s, 1H, CH), 7.65(d, 1H, CH), 8.18(d, 1H, CH) |
| I.13 | 2,4-dichloro | H | H | O | N—O | 137–140° C. |
| I.14 | 2,4-dichloro | H | H | NH | N—O | 143° C. |
| I.15 | 2,4-dichloro | H | H | O | CH—O | 112° C. |
| I.16 | 2,4-dichloro | H | CH$_3$ | O | N—O | 162° C. |
| I.17 | 2,4-dichloro | H | CH$_3$ | NH | N—O | 131° C. |
| I.18 | 2,4-dichloro | H | CH$_3$ | O | CH—O | 70° C. |
| I.19 | 3,4-dichloro | H | H | O | N—O | 118° C. |
| I.20 | 3,4-dichloro | H | H | NH | N—O | 186–188° C. |
| I.21 | 3,4-dichloro | H | H | O | CH—O | 141° C. |
| I.22 | 3,4-dichloro | H | CH$_3$ | O | N—O | 123° C. |
| I.23 | 3,4-dichloro | H | CH$_3$ | NH | N—O | 173° C. |
| I.24 | 3,4-dichloro | H | CH$_3$ | O | CH—O | 129–133° C. |

USE EXAMPLES

Examples of the Activity Against Harmful Fungi

The fungicidal activity of the compounds of the formula I was demonstrated by the following experiments:

The active compounds were prepared separately or jointly as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

The compounds A—C known from WO-A 97/24332 served as comparative compound

[Structure: pyrazole with (X)n-phenyl, O-linked phenyl with T-CH3, =O, YMe groups]

Table D

| No. | WO-A 97/24332 | (X)$_n$ | Y | T |
|---|---|---|---|---|
| A | D.003 | 4-Cl | O | CH—O |
| B | D.008 | 2,4-dichloro | NH | N—O |
| C | D.007 | 2,4-dichloro | O | N—O |

1) Protective Activity Against *Erysiphe graminis* var. *tritici* (Powdery Mildew of Wheat)

Leaves of potted weed seedlings cv. "Frühgold" were sprayed to runoff point with an aqueous active compound preparation which had been prepared from a stock solution comprising 10% of active compound, 63% of cyclohexanone and 27% of emulsifier, and, 24 hours after the spray coating had dried on, dusted with spores of powdery mildew of wheat (*Erysiphe graminis* forma specialis *tritici*). The test plants were subsequently placed in a greenhouse at from 20 to 22° C. and a relative atmospheric humidity of 75 to 80%. After 7 days, the extent of mildew development was determined visually as % infection of the total leaf area.

In this test, the plants treated with 16 ppm of the compound I.3 according to the invention showed an infection of 5%, while the plants which had been treated with 16 ppm of the comparative compound A showed an infection of 60% and the untreated plants (control) showed an infection of 80%.

2) Long-term Activity Against *Plasmopara viticola*

Leaves of potted grapevines cv. "Müller-Thurgau" were sprayed to runoff point with an aqueous active compound preparation which had been prepared from a stock solution comprising 10% of active compound, 63% of cyclohexanone and 27% of emulsifier. To assess the persistency of the substances, the plants were kept for 7 days in a greenhouse after the spray coating had dried on. Only then were the leaves inoculated with an aqueous zoospore suspension of *Plasmopara viticola*. The grapevines were then initially kept in a water vapor-saturated chamber at 24° C. for 48 hours and then in a greenhouse at 20–30° C. for 5 days. After this period of time, the plants were once more kept in a humid chamber for 16 hours to promote sporangiophore eruption. The extent of the infection on the undersides of the leaves was then assessed visually.

In this test, the plants treated with 16 ppm of the compound I.3 according to the invention showed no infestation, while the plants which had been treated with 16 ppm of the comparative compound A showed an infection of 40% and the untreated plants (control) showed an infection of 75%.

3) Protective Activity Against *pyricularia oryzae*

Leaves of potted rice seedlings cv. "Tai-Nong 67" were sprayed to runoff point with an aqueous active compound preparation which had been prepared using a stock solution of 10% of active compound, 63% of cyclohexanone and 27% of emulsifier. The next day, the plants were inoculated with an aqueous spore suspension of *pyricularia oryzae*. The test plants were subsequently kept in climatized chambers at 20–24° C. and 95–99% relative atmospheric humidity for 6 days. The extent of the infestation on the leaves was then determined visually.

In this test, the plants treated with 16 ppm of the the compound I.3 according to the invention showed an infestation of 15%, while the plants which had been treated with 16 ppm of the comparative compound A showed an infection of 60% and the untreated plants (control) showed an infection of 85%.

4) Activity Against *Botrytis cinerea* on Bell Pepper Leaves

After 4–5 leaves had developed properly, bell pepper seedlings c.v. "Neusiedler Ideal Elite" were sprayed to runoff point with an aqueous active compound preparation which had been prepared from a stock solution comprising 10% of active compound, 63% of cyclohexanone and 27% of emulsifier. The next day, the treated plants were inoculated with a spore suspension of *Botrytis cinerea* which contained $1.7 \times 10^6$ spores/ml in a 2% strength aqueous Biomalz solution. The test plants were subsequently placed in a climatized chamber at high atmospheric humidity and 22–24° C. After 5 days, the extent of the fungal infection on the leaves could be determined visually in %.

In this test, the plants which had been treated with 250 ppm of the compounds I.13 and I.14 according to the invention showed an infection of less than 40%, whereas the plants which had been treated with 250 ppm of the comparative compounds B and C and the untreated plants (control) were infected to almost 100% and 100%, respectively.

5) Curative Activity Against *Puccinia recondita* on Wheat (Brown Rust of Wheat)

Leaves of potted weed seedlings c.v. "Kanzler" were dusted with spores of Brown Rust (*Puccinia recondita*). The pots were then placed for 24 hours at from 20 to 22° C. in a chamber having high atmospheric humidity (from 90 to 95%). During this time, the spores germinated and the germ tubes penetrated into the leaf tissue. The next day, the infected plants were sprayed to run-off with an aqueous active compound preparation which had been prepared from a stock solution comprising 10% of active compound, 63% of cyclohexanone and 27% of emulsifier. After the spray coating had dried on, the test plants were cultivated in a greenhouse at 20–22° C. and 65–70% relative atmospheric humidity for 7 days. The extent of the Rust fungus development on the leaves was then determined.

In this test, the plants which had been treated with 16 ppm of the compound I.14 according to the invention showed no infection, whereas the plants which had been treated with 16 ppm of the comparative compounds B and the untreated plants (control) were infected to 40% and 80%, respectively.

Examples of the Activity Against Animal Pests

The Activity of the compounds of the formula I Against Animal pests was demonstrated by the following experiments:

The active compounds were prepared
a. as a 0.1% strength solution in acetone or
b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil)

and diluted with acetone in the case of a. or with water in the case of b. to the desired concentration.

After conclusion of the tests, the lowest concentration in each case was determined at which the compounds still caused 80–100% inhibition or mortality in comparison to untreated control tests (Activity threshold or minimum concentration).

We claim:

1. A compound of formula

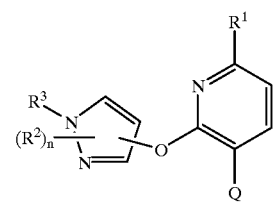

or a salt thereof, wherein

Q is —C(=CHCH$_3$)—COOCH$_3$, —C(=CHOCH$_3$)—COOCH$_3$, —C(=NOCH$_3$)—COOCH$_3$ or —C(=NOCH$_3$)—CONH(CH$_3$);

R$^1$ is hydrogen, halogen, C$_1$–C$_4$-alkyl, C$_1$–C$_2$-haloalkyl, C$_1$–C$_4$-alkoxy or C$_1$–C$_2$-haloalkoxy;

R$^2$ is halogen, C$_1$–C$_4$-alkyl, C$_1$–C$_2$-haloalkyl or C$_1$–C$_4$-alkoxy;

n is 0, 1 or 2, where the substituents R$^2$ are identical or different when n is 2;

R$^3$ is phenyl, pyridyl or pyrimidyl, where the phenyl, pyridyl or pyrimidyl radical is unsubstituted or carries one, two or three substituents selected from the group consisting of: halogen, cyano, C$_1$–C$_4$-alkyl, C$_1$–C$_2$-haloalkyl, C$_1$–C$_4$-alkoxy, C$_1$–C$_2$-haloalkoxy and C$_1$–C$_4$-alkoxycarbonyl.

2. A compound of formula Ia

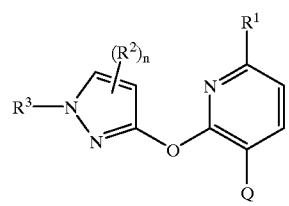

or a salt thereof, wherein

Q is —C(=CHCH$_3$)—COOCH$_3$, —C(=CHOCH$_3$)—COOCH$_3$, —C(=NOCH$_3$)—COOCH$_3$ or —C(=NOCH$_3$)—CONH(CH$_3$);

R$^1$ is hydrogen, halogen or halomethyl;

R$^2$ is chlorine, bromine, methyl or trifluoromethyl;

n is 0 or 1;

R$^3$ is phenyl, where the phenyl radical is unsubstituted or carries one, two or three substituents selected from the group consisting of: halogen, cyano, C$_1$–C$_4$-alkyl, C$_1$–C$_2$-haloalkyl, C$_1$–C$_4$-alkoxy, C$_1$–C$_2$-haloalkoxy and C$_1$–C$_4$-alkoxycarbonyl.

3. A compound of formula Ib

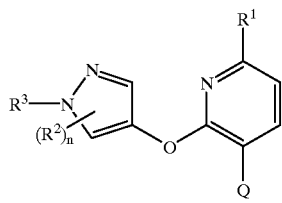

or a salt thereof, wherein
Q is —C(=CHCH$_3$)—COOCH$_3$, —C(=CHOCH$_3$)—COOCH$_3$, —C(=NOCH$_3$)—COOCH$_3$ or —C(=NOCH$_3$)—CONH(CH$_3$);
R$^1$ is hydrogen, halogen or halomethyl;
R$^2$ is chlorine, bromine, methyl or trifluoromethyl;
n is 0 or 1;
R$^3$ is phenyl, where the phenyl radical is unsubstituted or carries one, two or three substituents selected from the group consisting of: halogen, cyano, C$_1$–C$_4$-alkyl, C$_1$–C$_2$-haloalkyl, C$_1$–C$_4$-alkoxy, C$_1$–C$_2$-haloalkoxy and C$_1$–C$_4$-alkoxycarbonyl.

4. A composition suitable for controlling harmful fungi and animal pests, comprising an effective amount of the compound of formula I defined in claim 1 or a salt thereof and at least one formulation auxiliary.

5. A method for controlling harmful fungi animal pests, which comprises treating the harmful fungi or the animal pests, their habitat or plants, areas, materials or spaces to be kept free from the fungi or animal pests with an effective amount of the compound of formula I defined in claim 1 or a salt thereof.

6. The compound of formula I defined in claim 1, or the salt thereof, wherein
R$^1$ is hydrogen, halogen or halomethyl;
R$^2$ is chlorine, bromine, methyl or trifluoromethyl;
n is 0 or 1; and
R$^3$ is phenyl, where the phenyl radical is unsubstituted or carries one, two or three substituents selected from the group consisting of: halogen, cyano, C$_1$–C$_4$-alkyl, C$_1$–C$_2$-haloalkyl, C$_1$–C$_4$-alkoxy, C$_1$–C$_2$-haloalkoxy and C$_1$–C$_4$-alkoxycarbonyl.

7. The compound of formula I defined in claim 1, or the salt thereof, wherein the radical Q is —C(=CHOCH$_3$)—COOCH$_3$ or —C(=NOCH$_3$)—CONH(CH$_3$).

8. The compound of formula I defined in claim 1, or the salt thereof, wherein the radical

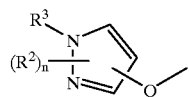

represents a group of formula

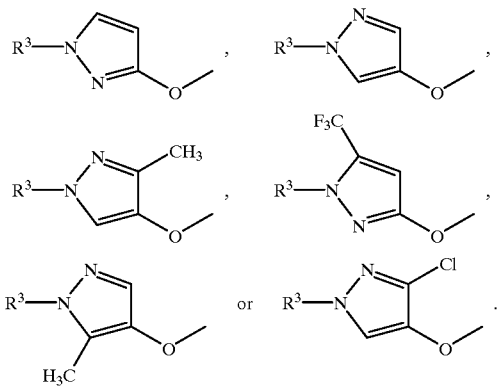

* * * * *